United States Patent
Kimball et al.

[11] Patent Number: 6,162,494
[45] Date of Patent: Dec. 19, 2000

[54] METHOD FOR MAKING AN OPTICAL SENSOR HAVING IMPROVED BARRIER PROPERTIES

[75] Inventors: Lynn M. Kimball, Rapid City, S. Dak.; Laura J. Bauer, Edina, Minn.; William V. Fowler, Minneapolis, Minn.; Laurie E. Lynch, Eden Prairie, Minn.

[73] Assignee: Optical Sensors, Inc., Minneapolis, Minn.

[21] Appl. No.: 09/538,316

[22] Filed: Mar. 30, 2000

Related U.S. Application Data

[62] Division of application No. 08/991,395, Dec. 16, 1997.
[51] Int. Cl.⁷ .................. B05D 5/06; C08F 2/04; C08F 2/50; G01N 21/64
[52] U.S. Cl. ............. 427/163.2; 427/2.12; 427/508; 427/510; 427/512; 427/514; 427/518; 427/519; 427/520; 427/157
[58] Field of Search .................. 427/163.2, 508, 427/510, 512, 514, 516, 518, 519, 520, 2.12, 157; 422/82.07

[56] References Cited

U.S. PATENT DOCUMENTS

| | | |
|---|---|---|
| 4,784,811 | 11/1988 | Hirschfeld .................. 264/1.27 |
| 4,785,814 | 11/1988 | Kane . |
| 4,798,738 | 1/1989 | Yafuso et al. .................. 427/2.11 |
| 4,842,783 | 6/1989 | Blaylock . |
| 4,919,891 | 4/1990 | Yafuso et al. . |
| 5,075,127 | 12/1991 | Yafuso et al. . |
| 5,354,825 | 10/1994 | Klainer et al. . |
| 5,607,644 | 3/1997 | Olstein et al. .................. 422/82.07 |
| 5,656,241 | 8/1997 | Seifert et al. . |
| 5,693,768 | 12/1997 | Backmann et al. . |
| 5,714,121 | 2/1998 | Alderete et al. .................. 422/82.07 |
| 5,728,422 | 3/1998 | Kane et al. .................. 427/163.2 |

FOREIGN PATENT DOCUMENTS

| | | |
|---|---|---|
| 0 263 693 | 4/1988 | European Pat. Off. . |
| WO 90/00572 | 1/1990 | WIPO . |

*Primary Examiner*—Shrive Beck
*Assistant Examiner*—Michael Cleveland
*Attorney, Agent, or Firm*—Dianne E. Reed; Reed & Associates

[57] ABSTRACT

A method for making a optical sensor for measuring the pH of a fluid includes the steps of applying a solution containing (a) a cellulose acrylamide, (b) an acrylamide, and (c) a copolymerizable monomeric fluorescent indicator species to the distal end of an optical fiber and polymerizing the solution to form a pH sensor means.

16 Claims, 1 Drawing Sheet

METHOD FOR MAKING AN OPTICAL SENSOR HAVING IMPROVED BARRIER PROPERTIES

CROSS-REFERENCE TO RELATED APPLICATIONS

This is a divisional of U.S. Ser. No. 08/991,395, filed Dec. 16, 1997, the disclosure of which is hereby incorporated by reference.

TECHNICAL FIELD

The present invention relates generally to optical sensors for measuring the pH of a fluid, and more particularly relates to a novel optical sensor system containing a membrane of a fluorescent cellulose acrylamide/acrylamide copolymer. The invention additionally relates to novel fluorescent polymer compositions and membranes made therefrom that may be used in the manufacture of optical sensors. One important application of the invention involves the accurate and precise measurement of pH in the physiological range in blood.

BACKGROUND

Chemical sensors are generally known for use in a wide variety of areas such as medicine, scientific research, industrial applications and the like. Fiber optic and electrochemical approaches are generally known for use in situations where it is desired to detect and/or measure the concentration of a parameter at a remote location without requiring electrical communication with this remote location. Structures, properties, functions and operational details of fiber optic chemical sensors can be found in U. S. Pat. No. 4,577,109 to Hirschfeld, U.S. Pat. No. 4,785,814 to Kane, and U.S. Pat. No. 4,842,783 to Blaylock, as well as Seitz, "Chemical Sensors Based on Fiber Optics," *Analytical Chemistry*, Vol. 56, No. 1, January 1984, each of which is incorporated by reference herein.

Publications such as these generally illustrate that it is known to incorporate a chemical sensor into a fiber optic waveguide, an electrochemical gas sensor or the like, in a manner such that the chemical sensor will interact with the analyte. This interaction results in a change in optical properties, which change is probed and detected through the fiber optic waveguide or the like. These optical properties of chemical sensor compositions typically involve changes in colors or in color intensities. In these types of systems, it is possible to detect particularly minute changes in the parameter or parameters being monitored in order to thereby provide especially sensitive remote monitoring capabilities. Chemical sensor compositions that are incorporated at the distal end of fiber optic sensors are often configured as membranes that are secured at the distal tip end of the waveguide device or optrode.

Sensors of this general type are useful in monitoring the pH of a fluid, measuring gas concentrations such as oxygen and carbon dioxide, and the like. Ion concentrations can also be detected, such as potassium, sodium, calcium and metal ions.

A typical fiber optic pH sensor positions the sensor material at a generally distal location with the assistance of various different support means. Support means must be such as to permit interaction between the pH indicator and the substance being subjected to monitoring, measurement and/or detection. With certain arrangements, it is desirable to incorporate membrane components into these types of devices. Such membrane components must possess certain properties in order to be particularly advantageous. Many membrane materials have some advantageous properties but also have shortcomings. Generally speaking, the materials must be biocompatible, hemocompatible for use in the bloodstream and selectively permeable to hydrogen ions.

It is also desirable to have these membrane materials be photocurable (such that curing is easier, can be done more rapidly, oil a smaller scale, and directly on the optical fiber) and resistant to shear forces (e.g., as present in a bloodstream. It is also preferred, clearly, that a signal oil sufficient intensity be produced, such that measurement is as accurate as is reasonably possible. It is additionally desired that the materials used for the sensor membrane be constructed such that pH values in a physiologic blood range may be accurately measured, and that the response time for measuring pH values is relatively rapid. An additional desirable property of a sensor for monitoring pH in blood or other physiologic fluid is that the sensor has minimal sensitivity to interfering substances. The optical pH sensors that are currently available are frequently inadequate with regard to one or more of the aforementioned criteria.

The present invention is addressed to a novel fluorescent polymer composition that is particularly suitable for use as a membrane and a membrane like component in an optical pH sensor and which provides for optical sensors which meet each of the above-mentioned criteria. That is, optical sensors as provided herein provide for good signal intensity, are rapidly cured with light, and are resistant to shear forces such as those present in flowing blood. In addition, pH sensors prepared using the novel polymer compositions have enhanced barrier properties such that the sensor is minimally sensitive to contaminating substances.

OVERVIEW OF RELATED ART

The following references relate to one or more aspects of the preset invention:

U.S. Pat. No. 4,785,814 to Kane describes an optical probe useful for measuring pH and oxygen and blood. The device includes a membrane constructed of a hydrophilic porous material containing a pH-sensitive dye.

U.S. Pat. No. 4,842,783 to Blaylock describes a fiber optic chemical sensor which, at the distal end of the optical fiber, is provided with a photocrosslinked polymeric gel having a dye adsorbed therein.

U.S. Pat. Nos. 4,919,891 and 5,075,127 to Yafuso et al. describe a fiber optic sensor in which an indicator composition is encased in a cellulosic overcoat stated to protect and enhance the signal obtained.

U.S. Pat. No. 5,354,825 to Klainer et al., describes a fiber optic sensing device for measuring a chemical or physiological parameter of a body fluke or tissue, in which a polymer containing photoactive moieties is directly bound to the fiber optic tip.

PCT Publication No. WO 90/00572, inventors Boesterling et al., describe the use of a urethane or an acrylamide hydrogel for measuring pH and/or $pCO_2$ in a fluid. The hydrogels are prepared by reacting an isocyanate prepolymer with a derivatized azo dye, i.e., an absorbance dye which is a molecule containing either an amino or hydroxyl functionality.

European Patent Application Publ. No. 0 263 693 describes an optical fiber pH sensor comprising a dye-containing cellulose matrix on the optical surface of the fiber and a carbon-black impregnated overcoating applied over the matrix.

H. J. Hageman et al., "Photoinitiators and Photocatalysts for Various Polymerisation and Crosslinking Processes," in *Radiation Curing of Polymers II*, ed. D. R. Randell (The Royal Society of Chemistry, 1991), at pp. 45–53, identify a number of materials which will act to catalyze radiation curing of multifunctional monomers or oligomers.

SUMMARY OF THE INVENTION

Accordingly, it is a primary object of the invention to address the above-mentioned needs in the art, by providing an optical sensor for measuring td pH of a fluid, which sensor gives rise to the numerous advantages identified above.

It is another object of the invention to address these needs by providing a fluorescent polymer composition for incorporation into such an optical sensor, wherein the fluorescent polymer composition comprises copolymer of a cellulose acrylamide, acrylamide and a polymerizable monomeric fluorescent indicator.

It is still another object of the invention to provide a membrane fabricated from cellulose acrylamide and, optionally, from a copolymer of cellulose acrylamide, acrylamide and/or a polymerizable monomeric fluorescent indicator.

It is yet another object of the invention to provide novel optical sensors comprising a pH sensor means comprising the fluorescent polymer composition.

It is a further object of the invention to provide a method for making an optical sensor containing the aforementioned fluorescent composition by polymerizing the composition on the fiber optic tip.

Additional objects, advantages and novel features of the invention will be set forth in part in the description which follows, and in part will become apparent to those skilled in the art upon examination of the following, or may be learned by practice of the invention.

In one aspect, then, a fluorescent polymer composition is provided which is useful in an optical sensor for the measurement of pH in a fluid sample. The fluorescent polymer composition comprises a copolymer of (a) cellulose acrylamide, (b) acrylamide, and (c) a polymerizable monomeric fluorescent indicator species. The ratio of the cellulose acrylamide to acrylamide and the ratio of cellulose acrylamide/acrylamide to the fluorescent species is determined to provide the composition with a predetermined apparent pKa. Generally, it is preferred that the ratio be such that the apparent pKa of the composition is in the range of about 6.6 to 8.0, more preferably in the range of about 7.2 to 7.8, most preferably in the range of about 7.2 to 7.4, which in turn optimizes the composition for use in measuring pH in the physiological range. The copolymer has the structure:

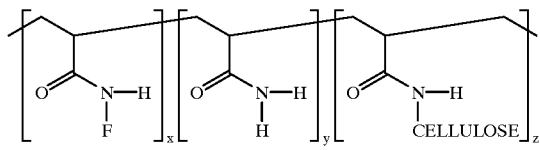

wherein:
F is the fluorescent indicator species;

CELLULOSE has the structure

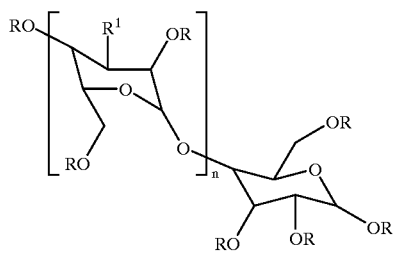

wherein each R is independently selected from the group consisting of H, $C_1$ to $C_6$ alky, $C_1$ to $C_6$ alkenyl, $C_1$ to $C_6$, alkynyl, and $C_1$ to $C_6$ esters, and $R_1$ is the acrylamide linkage to the copolymer backbone, —OR or $CH_2$=CH—(CO)—NH—;
n is in the range of about 2 to about 500;
x is in the range of about 1 to 30,000;
y is in the range of about 1,000 to 50,000,000;
z is in the range of about 1 to 1,000,000.

In another aspect, a selectively $H^+$-permeable membrane is provided which is useful for fabricating an optical pH sensor. The membrane comprises a copolymeric matrix of the novel fluorescent composition.

In still another aspect, an optical sensor is provided for the measurement of pH in a fluid sample, comprising an optical waveguide to receive light from a light source, and a pH-sensitive medium disposed on the waveguide which fluoresces in response to light from the light source, wherein the intensity of fluorescence is dependent on the pH of the environment being monitored, and the pH-sensitive medium comprises the aforementioned fluorescent polymer composition.

In a further aspect of the invention, an optical sensor is provided as described above further comprising a membrane of cured cellulose acrylamide/acrylamide copolymer applied as an overcoat to the fluorescent polymer composition.

In still a further object of the invention, a method for making an optical sensor for measuring the pH of a fluid is provided. The method comprises providing an optical waveguide having a distal end portion for contacting the fluid, and a proximal end portion for communication with means for receiving a signal from said distal end portion, coating said distal end portion with a solution containing the aforementioned fluorescent polymeric composition, and effecting polymerization of the solution to form a pH sensor means.

In yet a further aspect of the invention, a method for making a fiber optic sensor is provided which involves sequentially providing two or more layers of material at the tip of an optical fiber. The innermost layer is an adhesive layer which adheres to the exposed fiber surface and to a cladding material, if present. The adhesive layer may contain some sort of dye or indicator material, preferably a substantially analyte-insensitive reference dye, and comprises a polymeric material which is partially or fully cured prior to application of additional layers. Overlaying this adhesive layer is a further layer, containing analyte-sensitive materials, also sometimes termed herein the "sensing chemistry." Additional layers may in some cases be present; whether or not such layers are included will depend on a number of factors, e.g., on the end use of the sensor, the materials involved in the "sensing chemistry," and the like. The configuration of the inner adhesive layer controls the geometry of the sensing layer applied thereto, and can be manipulated to obtain optimum sensor signal strengths and adhesion. It allows sensors to be manufactured in which there is excellent mechanical adhesion and, optionally, covalent bonding, between the adhesive and sensing layers. The mechanical adhesion results from the deposition of the sensing layer directly on the inner adhesive material, the geometry of the sensing and adhesive layers, and the materials selected for these layers.

BRIEF DESCRIPTION OF THE DRAWINGS

In the course of this description, reference will be made to the attached drawing, wherein.

DETAILED DESCRIPTION OF THE INVENTION

Figure 1:
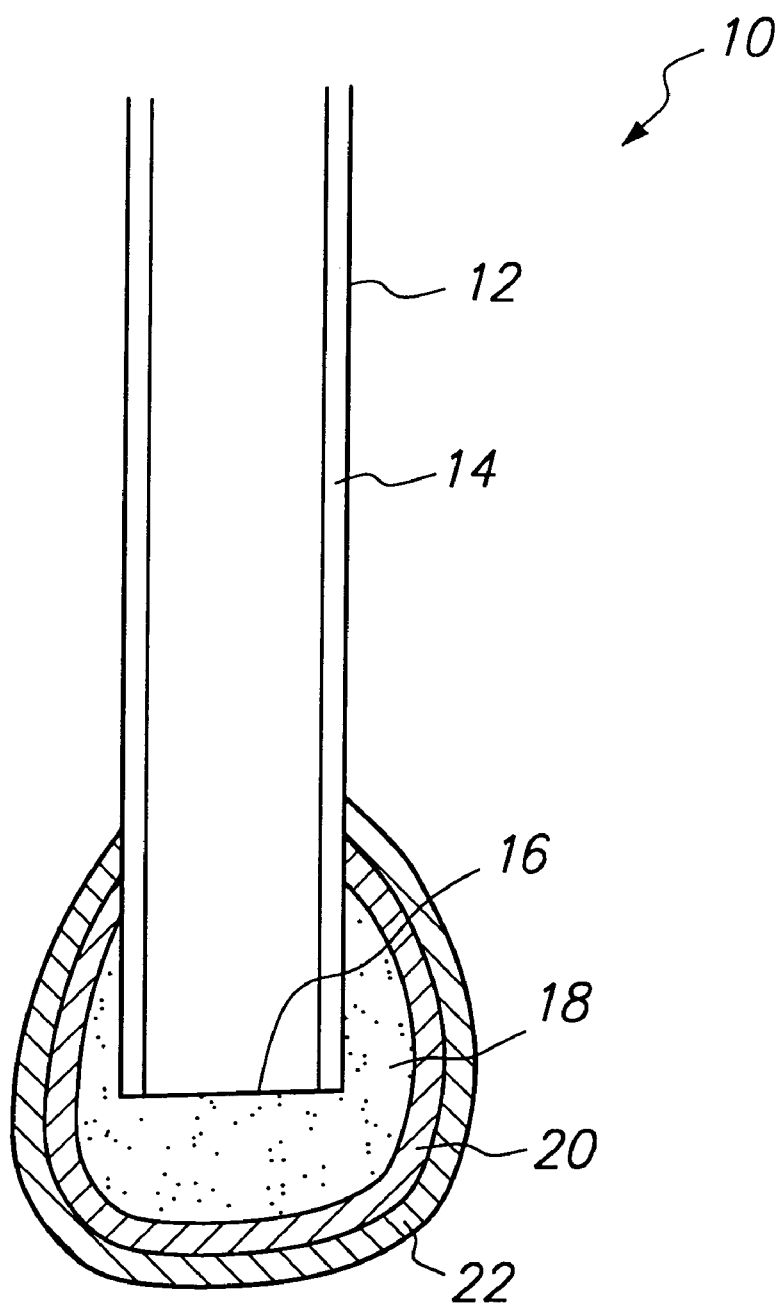
FIG. 1 is a generally schematic view of the sensing tip of a fiber optic device manufactured using the compositions and techniques of the present invention.

Before the present sensors and methods are disclosed and described, it is to be understood that this invention is not limited to specific sensor formats, specific indicator compositions, or particular adhesives, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an indicator material" includes mixtures of suitable indicator materials, reference to "an adhesive material" includes mixtures of two or more adhesives, reference to "an adhesive layer" or "an inner adhesive layer" includes two or more adhesive layers, reference to "a sensing layer" or "an outer sensing layer" includes two or more sensing layers, reference to "an indicator material" includes mixtures of suitable indicator materials, reference to "a reflective material" includes mixtures of two or more reflective materials, reference to "a wavelength" includes more than one wavelength, and the like.

In describing and claiming the present invention, the following terminology will be used in accordance with the definitions set out below.

The term "optical fiber means" is used herein to refer to a single optical fiber or a bundle of optical fibers. Suitable materials for optical fibers will be outlined below.

The term "sample fluid" as used herein refers to a liquid or gaseous material which may be analyzed using the presently disclosed sensors, either with respect to a parameter such as pH, or with regard to the presence or concentration of gases such as oxygen, carbon dioxide, or the like. Generally, "sample fluids" analyzed using the sensors manufactured herein will be physiological fluids such as blood.

The term "indicator" as in "indicator composition," "indicator material" or "indicator component" refers to a species which is sensitive to a parameter of interest in the sample undergoing analysis. For example, an oxygen indicator will generally be an organic and/or organometallic chemical compound which, when exposed to an appropriate wavelength of light, emits a measurable fluorescence signal which is sensitive to (i.e., quenched by) the oxygen to which it is exposed. For measuring pH, the indicator will generally be a fluorescent dye or some other fluorescent material which is pH-sensitive.

The terms "reference material" or "reference dye" intends a species which is substantially insensitive to the parameter of interest in the sample undergoing analysis, and will be used in conjunction with an indicator material. For example, reference dyes used in conjunction with oxygen sensors will typically be chemical compounds which, when exposed to a particular wavelength of light, emit a measurable fluorescence signal which is substantially insensitive to (i.e., not significantly quenched by) oxygen.

The term "sensing chemistry" as used herein refers to a composition containing components which in combination enable measurement of the parameter of interest in a sample fluid. For example, "pH sensing chemistry" intends a composition containing chemical components which enable measurement o)f pH.

The term "polymer" as used herein is intended to include both oligomeric and polymeric materials, i.e., compounds which include two or more monomeric units. The term is also intended to include "copolymeric" materials, i.e., containing two or more different monomeric units.

The term "acrylamide" is used herein in its conventional sense to denote photopolymerizable organic compounds containing a recurring

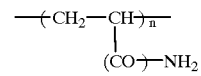

linkage. The term "cellulose acrylamide" is intended to mean a photopolymerizable cellulose polymer having pendent acrylamide moieties. The "degree of substitution" of a cellulose acrylamide is intended to refer to the average number of acrylamide moieties per cellulose repeat unit. Thus, a degree of substitution of 0.25% intends that, on the average, there is one acrylamide moiety for every 400 cellulose repeat units.

The term "precursor" is used herein to mean a composition which when polymerized will give rise to a desired polymer. For example, the term "cellulose acrylamide-acrylamide pre-polymer" denotes a composition which when treated with, e.g., radiation or heat and an initiator with or without added crosslinking agents, or combinations thereof, will give rise to a "cellulose acrylamide polymer" as will be described in greater detail below.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkenyl" as used herein refers to a branched or unbranched hydrocarbon group of 2 to 24 carbon atoms containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the liked Preferred alkenyl groups herein contain 2 to 12 carbon atoms and 2 to 3 carbon-carbon double bonds. The term "lower alkenyl" intends an alkenyl group of 2 to 6 carbon atoms, preferably 2 to 4 carbon atoms, containing one —C=C— bond.

The term "alkynyl" as used herein refers to a branched or unbranched hydrocarbon group of 2 to 24 carbon atoms containing at least one —C≡C— bond, such as ethynyl, n-propynyl, isopropynyl, n-butynyl, isobutynyl, t-butynyl, octynyl, decynyl and the like. Preferred alkynyl groups herein contain 2 to 12 carbon atoms. The term "lower alkynyl" intends an alkynyl group of 2 to 6, preferably 2 to 4, carbon atoms, and one —C≡C— bond.

The term "ester" as used herein intends a moiety having the structure R'C(O)O— in which R' is an alkyl, alkenyl or alkynyl group. A "$C_1$ to $C_6$ ester" is an ester in which R' is a $C_1$ to $C_6$ alkyl, a $C_1$ to $C_6$ alkenyl or a $C_1$ to $C_6$ alkynyl.

"Optional" or "optionally" means that the subsequently described circumstance may or may not occur, and that the description includes instances in which said circumstance occurs and instances in which it does not. For example, the phrase "optionally including an reflective material" means that a reflective material may or may not be present, and the description includes both the instance when the reflective material is present and the instance when the reflective material is not present.

At the outset, a fluorescent polymeric composition is provided useful in an optical sensor for the measurement of pH in a sample. In addition, the composition may be used to form membranes that may be used to form am optical pH sensor to monitor sample pH. The composition comprises cellulose acrylamide, acrylamide, and a copolymerizable monomeric species.

Cellulose acrylamide has the structure:

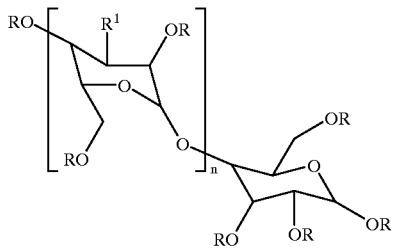

wherein R, $R_1$ and n are as defined above. The fractional degree of substitution, based on the number of acrylamide moieties per repeat unit of cellulose chain, i.e., when $R_1$ is CH=CH—C(O)—NH—, is in the range of about 0.001 to about 0.33, preferably about 0.001 to about 0.2, more preferably about 0.001 to about 0.1. Preferred R groups include H and $C_1$ to $C_6$ esters. The number of monomer units, n, is in the range of about 3 to about 500, and is selected generally such that a 20% solution of the cellulose in methyl ethyl ketone has a viscosity at 25° C. in the range of about 10 to about 250 centipoise, preferably in the range of about 150 to about 250 centipoise.

The pH-sensitive indicator material may be virtually any fluorescent dye or material that is sensitive to pH. In one embodiment, the fluorescent indicator is physically entrapped within the polymeric matrix. Examples of fluorescent dyes that may be entrapped within the polymeric matrix include fluorescein, carboxyfluorescein, fluorescein isothiocyanate polymer conjugates, coumarin, seminaphtharhodafluorescein, seminaphthafluorescein, naphthafluorescein, aminopyrene trisulfonic acid (APTS), hydroxypyrene trisulfonic acid (HPTS), dichlorofluorescein, and fluorescein salts such as lithium fluoresceinate. Preferably, the pH-sensitive indicator material is fluorescein, APTS or HPTS. In another embodiment, the fluorescent indicator is modified to enable copolymerization with the cellulose acrylamide and acrylamide prepolymer. Exemplary preferred modified fluorescent dyes are typically although not necessarily selected from the group consisting of acryloyl derivatives of the fluorescent dyes listed above. Preferably, the copolymerizable pH-sensitive indicator material is fluorescein acrylamide, APTS acrylamide or HPTS acrylamide. The fluorescent polymeric composition will typically contain on the order of about 0.01 wt. % to 1.0 wt. % fluorescent dye. The copolymer has the structure:

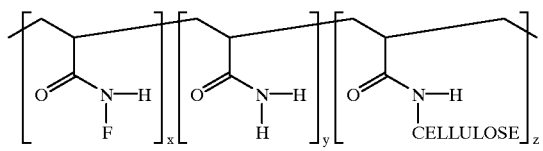

wherein F, CELLULOSE, x, y, and z are as defined above.

A base prepolymer composition is prepared by mixing cellulose acrylamide and/or acrylamide in a suitable solvent. The pH sensing chemistry solution is prepared by admixing the fluorescent monomer species and a photoinitiator, if desired, with the prepolymer solution. The total amount of the dissolved solids is typically in the range of about 20% to 80% by weight. Generally, the polymer composition solution will contain on the order of about 5 to about 60 wt. %, preferably about 20 to about 30 wt. % cellulose acrylarnide, about 5 to about 60 wt. %, preferably about 20 to about 30 wt. % acrylamide, about 0.01 to 5.0 wt. %, preferably about 0.05 to about 0.5 wt. % copolymerizable fluorescent indicator species; and/or about 0.05 to about 5.0 wt. %, preferably 0.1 to about 1.0 wt. % photoinitiator. Preferred solvents include water-miscible, low boiling point solvents such as methanol and ethanol, and partially water-miscible solvents such as ethyl acetate. Water-miscible, polar solvents that have higher boiling points may also be used, such as dimethylsulfoxide, dimethylformamide, N-methylpyrrolidone, dimethylacetamide, or the like. A preferred high boiling point solvent is dimethylsulfoxide used at about 20% to 80% by weight.

Suitable photoinitiators are radical photoinitiators that are well known to those skilled in the art. Examples of such photoinitiators include α-alkoxy deoxybenzoins, α,α-dialkoxy deoxybenzoins, α,α-dialkoxy acetophenones, 2-hydroxy-2,2-dialkyl acetophenones, benzophenones, thioxanthones, benzils, and other compounds identified by H. J. Hageman et al., "Photoinitiators and Photocatalysts for Various Polymerisation and Crosslinking Processes," in *Radiation Curing of Polymers II*, ed. D. R. Randell (The Royal Society of Chemistry, 1991), at pp. 46–53, cited supra. The disclosure of the aforementioned reference is incorporated by reference herein. One particular preferred commercially available photoinitiator is Darocur® 1173 (Ciba-Creigy, Hawthorne, N.Y.)

Suitable crosslinking agents such as N',N-methylene bisaciylamide or other diacrylamides or dimethacrylamides, diacrylates, or dimethacrylates may also be used in small amounts, e.g., about 0.1% to 10% by weight, preferably about 0.3% to 3% by weight.

Preparation of a membrane comprising cellulose acrylamide, acrylamide and/or a fluorescent indicator dye may be accomplished using techniques well known in the art. The membrane may be prepared as a film using conventional solvent casting techniques. Alternatively, the membrane may be prepared as a polymerized film. Such a polymerized film may be formed by preparing a polymeric composition containing cellulose acrylamide, acrylamide and/or the fluorescent indicator species or copolymerizable fluorescent indicator species, and admixing the polymeric composition with an initiator in a suitable solvent. The composition is then formed into a film and radiation or health cured to form a membrane.

Preparation of an optical pH sensor comprising the aforementioned pH sensing chemistry solution may be accomplished using any method known in the art. An optical fiber means is provided which serves to communicate optical signals from a sample fluid to a detection means. The optical fiber means will typically comprise a single elongated optical fiber, although it may comprise a bundle of optical fibers associated in parallel.

Examples of suitable fiber substrate materials include glass, plastic, glass/glass composite and glass/plastic composite fiber waveguides. A critical characteristic of optical fibers is attenuation of the optical signal. Thus, glasses which contain unacceptable levels of transition-metal impurities when prepared from naturally occurring materials lead to high absorption losses. Silica fibers of acceptable quality can be prepared from purified starting materials (e.g., silicon tetrachloride and germanium tetrachloride) using conventional glass-melting techniques of drawing into fibers.

Generally, although not necessarily, the fiber will be provided with a cladding means. As will be appreciated by those skilled in the art, the cladding means serves to provide structural support for an otherwise fragile fiber, and also provides a coating which guides light conducted along the fiber. In the present case, the cladding means typically comprises a fluoropolymer such as polymeric fluoroacrylate. However, the cladding means may also be comprised of glass, or it may be comprised of polystyrene, polyimide or any other suitable plastic material.

One preferred method of preparing an optical sensor for measuring pH of a fluid sample is described in commonly owned U.S. Pat. No. 5,607,644 to Olstein et al., the disclosure of which is incorporated herein by reference in its entirety.

According to this method, the optical sensors of the invention are prepared by first making the pH sensing chemistry solution, as described above. The pH sensing chemistry solution is applied to the distal end of an optical fiber by coating, painting, dipping, or the like, and then cured on the fiber. Alternatively, the pH sensing chemistry solution may be cured first and then affixed to the fiber optic tip. However, the former method is preferred.

Curing may be carried out by exposing the aforementioned sensing solution, preferably in the form of a coating on the fiber optic tip, to radiation of a wavelength effective to initiate copolymerization. In a particularly preferred embodiment, curing is carried out on the fiber substrate using radiation transmitted external to the fiber, i.e., after a solution containing the cellulose acrylamide polymer, acrylamide monomer, initiator, solvent and the fluorescent monomeric species has been provided on the fiber tip by coating, painting, dipping, or the like. In an alternative embodiment, curing is carried out on the fiber substrate by using radiation transmitted through the fiber. Optionally, crosslinkers may be added to the pH sensing chemistry solution prior to curing.

With glass fibers, it has typically been necessary to prime the fiber surface prior to photopolymerization or deposition of the sensing membrane thereonto. An example of a suitable glass primer is γ-methacryloxypropyl trimethoxysilane. Once cured, the sensor thus formed may be cleaned of residual unreacted monomer by soaking in an innocuous solvent such as dim ethylsulfoxide.

A second preferred method of manufacturing a fiber optic sensor is that described in commonly owned U.S. Pat. No. 5,656,241, to Seifert et al., the disclosure of which is incorporated herein by reference in its entirety. For purposes of completeness, the following is a brief description of the method of manufacture described in the aforementioned document.

Prior to deposition of the adhesive layer, the fiber tip region may, if desired, be pretreated, for example, by rinsing or washing, or by activation using any number of techniques (e.g., corona, plasma, etching, or the like). Other surface treatment methods may also be used if desired; generally such methods will be selected to enhance the adhesion of the innermost layer.

The innermost layer is deposited on the tip of the fiber typically using a simple dip coating procedure. This layer comprises an adhesive material, preferably a photocurable adhesive material. A wide variety of adhesive materials can be used, so long as sufficient adhesion is provided between the fiber or cladding material and the layer or layers containing the sensing chemistry. It is also necessary that the materials of the innermost layer be physically and chemically compatible with other materials used to construct the sensor and, clearly, with any other components incorporated into the innermost layer itself, e.g., reference dyes or the like.

Examples of preferred adhesive materials include, but are not limited to, polyurethanes, polyurethane precursors, acrylated polyurethan, acrylated polyurethane precursors, acrylates, epoxy resins, acrylated epoxy resins, and silicones, with urethane-based and urethane acrylate adhesives particularly preferred. Radiation curable materials are generally preferred as well, as noted above, although materials which may be cured using alternative techniques may also be used, e.g., moisture-curable or heat-curable adhesives.

Examples of specific commercially available adhesives which can be used to prepare the innermost layer herein include the following: the urethane-based adhesives Airthane®, Polathane®, Ultracast® and Cyanaprene® (Air Products and Chemicals, Inc.), as well as Conathane® (Conap, Inc.), Rubinate® (ICI Polyurethanes Group), and Jedbond® (Jedco Chemical Corp.); radiation-clirable aliphatic and aromatic urethane acrylates and epoxy acrylates available from Sartomer Co., Inc. under the tradenames CN 950, 960, 970, 980, 104, 111, 114 and 120; urethane acrylates available under the trademark Purelast® from Polymer Systems Corp.; urethane acrylates 3321, 3311, 3211 and 3301 available from Loctite; acrylate and methacrylate epoxies and urethanes available from Echo, Inc.; and epoxy and urethane acrylates available from Cargill, Inc., and the radiation-curable acrylic resins available under the trademarks Tritherml®, Terasod® Pedigreed® and Soderite® from the P.D. George Co.

Other components may be incorporated into the adhesive layer as well, typically any materials that are compatible with the adhesive, the components of the outer, sensing layer or layers, and the fiber or cladding material. The adhesive layer may, for example, contain a cross-linking agent to facilitate curing. Alternatively, or in addition, the adhesive layer can be used to incorporate one of two dye materials used in analyte measurement. When two dyes are used in a particular type of measurement, e.g., a species-sensitive indicator material and a species-insensitive reference dye, it may be desirable to incorporate the reference dye into the innermost layer to enhance signals and/or minimize contact with analyte.

The geometry of the adhesive layer(s) determines the geometry of the pH sensing layer(s). In this manner, the amount of the adhesive deposited can be easily manipulated to produce the desired amount pH sensing chemistry.

It may be desirable to mold or form the inner adhesive layer prior to curing, to change the geometry of the tip, again, typically to optimize the surface area to which additional layers bind. In this way, as with the use of multiple adhesive layers, it becomes possible to mechanically bind the sensing layer or layers to the fiber tip.

Generally, the thickness of the adhesive present at the fiber optic tip will be in the range of about 15 to about 300 microns.

The adhesive layer is then partially or fully cured, using moisture, heat, or, preferably, ultraviolet radiation (alternatively, curing may, in some cases, occur simply with the passage of time). With ultraviolet curing, the coated tip is exposed to radiation of a predetermined wavelength, and for a time and at an intensity selected to effect the desired degree of curing. The coated tip is preferably exposed to ultraviolet light in a uniform manner, and preferably from an external source rather than through the fiber. It may in some cases be desirable to cure the innermost layer only partially, such that a reactive surface is provided, in turn enabling covalent binding of the next layer of material. With a fully cured innermost layer, the next layer will adhere mechanically rather than chemically; with a partially cured innermost layer, adhesion of the next layer may be both chemical and mechanical.

After the innermost layer is provided on the fiber tip, formed into a desired geometry, and partially or fully cured, additional adhesive layers may be provided, followed by deposition of a subsequent layer. The fluorescent polymeric composition solution as described above, which contains the "sensing" materials necessary to conduct the desired measurement of pH are then applied as a layer over the outermost adhesive layer. Additional sensing layers may, if desired, be present.

The sensing layer will contain the "sensing chemistry" necessary for the device to be used in-measuring pH. Optionally, the initial sensing layer will serve as an intermediate layer, with an additional sensing layer present which has a chemical composition identical to that of the initial sensing layer. As described above, the sensing layer or layers will be formulated from a fluorescent polymer composition solution comprising a copolymer of (a) a cellulose acrylamide, (b) acrylamide, and (c) a copolymerizable monomeric fluorescent indicator species, prepared as described above.

The fiber tip, having the inner adhesive layer already present, is then coated with the aforementioned solution, typically using a similar dip coating technique used to provide the adhesive, so as to give rise to an outer layer containing the sensing chemistry. Curing is then conducted as described with respect to the adhesive layer, using ultraviolet radiation of one or more predetermined wavelengths and intensities.

After the initial sensing layer is provided, it is then optional, although not essential, to provide a further sensing layer, identical to the initial layer, using the same methodology. Each of the sensing layers will generally be in the range of about 10 to about 50 microns in thickness.

Once prepared, with the layers described above having been cured, the pH sensor is then stored in an aqueous solution, preferably saline, to hydrate the sensor coating prior to use.

It may also be desirable to apply a coating over the sensor chemistry using either of the two above-described methods of preparing the sensor. The overcoating layer comprises a solution of a polymeric composition comprising a cellulose acrylamide and acrylamide. The solution is prepared by admixing the polymeric composition with a photoinitiator in a suitable solvent, as described above with respect to the preparation of the pH sensing chemistry solution. The ranges of amounts of the cellulose acrylamide, acrylamide and photoinitiator are as described above with respect to the pH sensing chemistry solution.

The fiber tip, having the inner adhesive layer and outer sensing chemistry layer already, present, is then coated with the aforementioned overcoating solution, typically using similar dip coating and curing techniques used to provide the adhesive and sensing chemistry layers, so as to give rise to an overcoat layer.

It may also be desirable to incorporate a reflective material into the sensor. The reflective material may be incorporated into the sensing matrix or, when present, into the overcoat material. In the former case, particles of a selected reflective material are admixed with the matrix precursors (i.e., the reactants used to provide the final fluorescent polymeric composition). Suitable reflective materials include titanium dioxide, zinc oxide and barium sulfate, with titanium dioxide particularly preferred. Generally, the fluorescent polymeric composition or the overcoat matrix so prepared will contain on the order of 0.01 wt. % to 20 wt. % reflective material, preferably in the range of about 0.1 wt. % to 10 wt. %, most preferably in the range of about 1 wt. % to 10 wt. %. Particle size is not critical, but will generally be on the order of approximately 0.1 to 1000 nm in diameter, preferably on the order of approximately 200 nm to 800 nm in diameter, and most preferably on the order of approximately 300 nm to 500 nm in diameter.

In FIG. 1, sensor 10 is shown substantially as prepared by the method described in U.S. Pat. No. 5,656,241, with the fiber shown as element 12, having cladding 14 present thereon and an exposed core 16, inner adhesive layer 18 deposited around the fiber tip region, sensing chemistry layer 20 deposited over the adhesive layer and overcoat layer 22 deposited over the sensing chemistry layer.

Sensors for monitoring pH in a sample fluid prepared as described herein have excellent barrier properties, as well as high signal-to-noise ratios and rapid response times. The membranes and the sensors prepared therefrom, are inexpensive and easy to manufacture, and are robust to steam sterilization.

It will be appreciated by those working in the art that sensors fabricated using the presently disclosed and claimed techniques may be used in a wide variety of contexts. That is, while the invention has primarily been described in conjunction with the measurement of pH in blood, the sensors fabricated using the present method may be used to evaluate any number of sample types in a variety of industries, including fermentation technology, cell culture, and other biotechnology applications.

Thus, it is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

EXPERIMENTAL

The following examples are put forth so as to provide those of ordinary skill in the art with a complete disclosure and description of how to make and use the compounds of the invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

All solvents were purchased as HPLC grade and, where appropriate, solvents and reagents were analyzed for purity using common techniques.

EXAMPLE 1

PREPARATION OF PRE-POLYMER SOLUTION

The objective of this example was to prepare the cellulose acrylamide/acrylamide pre-polymer solution used in blending pH sensitive chemistry solutions and overcoat chemistry solution, which when polymerized produce membranes with enhanced resistance to interfering substances.

A solution of pre-polymer was prepared containing the following components: 25 wt. % cellulose acrylamide (Monomer-Polymer and Dajac Laboratories, Inc., Trevose, Pa.), 25 wt. % acrylamide (Aldrich, Milwaukee, Wis.) and 50 wt. % dimethylsulfoxide (Aldrich, Milwaukee, Wis.). This pre-polymer solution is referred to as the "CACAC" solution.

EXAMPLE 2

PREPARATION OF A pH SENSING CHEMISTRY SOLUTION

The objective of this example was to prepare a pH sensing chemistry solution which when polymerized produces a pH sensitive membrane with enhanced resistance to interfering substances.

A solution of pH sensing chemistry was prepared by admixing the following components: 0.5 g CACAC solution, 15 $\mu$l of a 3.5 wt. % solution of fluorescein acrylamide (FLAC) (Optical Sensors Inc., Minneapolis, Minn.) in dimethylsulfoxide and 2.5 $\mu$L Darocur® 1173 (Ciba-Geigy, Hawthorne, NY).

EXAMPLE 3

PREPARATION OF A pH SENSING CHEMISTRY SOLUTION CONTAINING A REFLECTIVE MATERIAL

The objective of this example was to prepare a pH sensing chemistry solution similar to that prepared in Example 2 with the incorporation of a reflective material to enhance signal levels.

A solution was prepared as described in Example 2 with the addition of 15 $\mu$l of a 50 wt. % solution of titanium dioxide in diniethylsulfoxide.

EXAMPLE 4

PREPARATION OF AN OVERCOAT CHEMISTRY SOLUTION

The objective of this example was to prepare an overcoat chemistry solution which when polymerized produces a membrane with barrier properties to minimize the influence of interfering substances on the ability to monitor pH.

A solution of overcoat chemistry was prepared by admixing the following components: 0.5 g CACAC and 2.5$\mu$l Darocur® 1173.

EXAMPLE 5

PREPARATION OF A pH SENSOR WITHOUT AN OVERCOAT

The objective of this example was to prepare a pH sensor having a cured inner layer of an acrylated urethane adhesive and an outer layer containing pH sensing chemistry.

The fiber used was HCN/H High NA HCS containing a hard polymer cladding bonded to a pure silica core (Spectran Specialty Optic, Avon, Conn.). The fiber was pre-treated by washing in ethanol followed by air drying. Loctite adhesive 3211 was placed in a well. The fiber was placed into a holder and lowered into the adhesive to coat the tip. The fiber was raised from the adhesive-containing well and the adhesive-coated fiber was cured under nitrogen with an Oriel mercury arc lamp.

The fiber having the cured adhesive layer thereon was then lowered into a well containing the pH sensing chemistry solution, prepared as described in Example 3, until the adhesive was completely covered. The fiber was then raised from the pH sensing chemistry solution and cured under nitrogen with an Oriel mercury arc lamp.

All coating procedures were performed within a controlled environment containing less than 10% relative humidity at room temperature. The cured tip was then placed in a saline solution in order to hydrate and store the sensor prior to use.

The pH sensor so prepared was then evaluated for pH responsiveness and stability toward steam sterilization. Sensing chemistries remain attached following steam sterilization without deterioration in performance.

EXAMPLE 6

PREPARATION OF A pH SENSOR WITH AN OVERCOAT

The objective of this example was to prepare a pH sensor having a cured inner layer of an acrylated urethane adhesive, an intermediate layer containing pH sensing chemistry and an overcoat layer to provide additional protection against interfering substances.

Sensors were prepared as described in Example 5 with the following additions: following curing of the pH sensing chemistry solution on the fiber, the fiber was then lowered into a well containing the overcoat chemistry solution prepared as described in Example 4 until the pH sensing chemistry layer was completely covered. The fiber was then raised from the overcoat chemistry membrane solution and cured under nitrogen with an Oriel mercury arc lamp.

All coating procedures were performed within a controlled environment containing less than 10% relative humidity at room temperature. The cured tip was then placed in a saline solution in order to hydrate and store the sensor prior to use.

The pH sensor so prepared was then evaluated for pH responsiveness, stability toward steam sterilization and sample fluid shear forces. Sensing chemistries remain attached following steam sterilization and exposure to excessive shear forces without deterioration in performance.

EXAMPLE 7

DEMONSTRATION OF pH SENSOR RESISTANCE TO BILIRUBIN INTERFERENCE WITH OR WITHOUT AN OVERCOAT

The objective of this example was to demonstrate the resistance of pH sensors to bilirubin interference. Control pH sensors were made with urethane acrylamide as the pre-polymer. Control pH sensors and CACAC pH sensors with and without an overcoat, were made and exposed to human blood spiked with conjugated bilirubin (Porphyrin Products, Logan, Utah). The testing method consisted of calibrating the pH sensors using aqueous buffer solutions.

All blood samples were tonometered with a gas mixture producing $pO_2$ of about 100 mm Hg, $pCO_2$ of about 40 mm Hg, and pH about 7.4. A total of at least three unspiked human blood samples were measured on each sensor. This human blood was then spiked to a certain level of conjugated bilirubin and additional measurements were made. All blood samples were measured using the OSI system which included the SensiCath, OpticalCAM, and ABG module.

The results are shown in Tables 1, 2, and 3 below, in which accuracy and precision are expressed in pH units.

TABLE 1

Control pH sensors (n = 2) tested at 30 mg/dl conjugated bilirubin

|  | TYPE→ | Spiked | Unspiked |
|---|---|---|---|
|  | COUNT→ | 8 | 6 |
| ACCURACY | measured | 0.087 | −0.002 |
| PRECISION | measured | 0.027 | 0.009 |

TABLE 2

CACAC pH sensors (n = 4) with an overcoat tested at 40 mg/dl conjugated bilirubin

|  | TYPE→ | Spiked | Unspiked |
|---|---|---|---|
|  | COUNT→ | 200 | 12 |
| ACCURACY | measured | −0.013 | −0.022 |
| PRECISION | measured | 0.018 | 0.012 |

TABLE 3

CACAC pH sensors (n = 4) without an overcoat tested at 30 mg/dl conjugated bilirubin

|  | TYPE→ | Spiked | Unspiked |
|---|---|---|---|
|  | COUNT→ | 188 | 13 |
| ACCURACY | measured | 0.011 | −0.007 |
| PRECISION | measured | 0.016 | 0.007 |

In the tables, "count" refers to the total number of samples tested; the number of samples was evenly distributed between the sensors in each group. Control sensors demonstrated inaccuracies of 0.087 pH units following 4 samples of blood spiked with bilirubin. In comparison, CACAC sensors with and without overcoats were accurate to within 0.013 and 0.011 pH units, respectively, following 47 to 50 samples of blood spiked with bilirubin.

Thus, the invention provides novel optical sensors, novel fluorescent polymer compositions and membranes made therefrom. Although preferred embodiments of the subject invention have been described in some detail, it is understood that obvious variations can be made without departing from the spirit and the scope of the invention as defined by the appended claims.

We claim:

1. A method for making an optical sensor for measuring the pH of a fluid, comprising the steps of:
   (a) providing an optical waveguide having a distal end portion for contacting the fluid, and a proximal end portion for communication with means for receiving a signal from said distal end portion;
   (b) coating said distal end portion with a solution containing (i) a cellulose acrylamide, (ii) acrylamide and (iii) a copolymerizable monomeric fluorescent species; and
   (c) effecting polymerization of the solution to form a pH sensor means.

2. The method of claim 1, wherein the solution additionally comprises a photoinitiator.

3. The method of claim 2, wherein the photoinitiator is selected from the group consisting of α-alkoxy deoxybenzoins, α,α-dialkoxy deoxybenzoins, α,α-dialkoxy acetophenones, 2-hydroxy-2,2-dialkyl acetophenones, benzophenones, thioxanthones, and benzils.

4. The method of claim 2, wherein step (c) is carried out by irradiating said distal end portion with radiation of a wavelength effective to initiate polymerization.

5. The method of claim 4, wherein step (c) is carried out by irradiating through the optical waveguide.

6. The method of claim 1, wherein the copolymerizable monomeric fluorescent species is selected from the group consisting of acryloyl derivatives of fluorescein, carboxyfluorescein, fluorescein isothiocyariate polymer conjugates, coumarin, seminaphtharhodafluorescein, seminaphthafluoirescein, naphthafluorescein, aminopyrene trisulfonic acid (APTS), hydroxypyrene trisulfonic acid (HPTS), dichlorofluorescein, and fluorescein salts.

7. The method of claim 6, wherein the copolymerizable monomeric fluorescent species is fluorescein acrylamide.

8. The method of claim 6, wherein the copolymerizable monomeric fluorescent species is APTS acrylamide.

9. The method of claim 1, wherein the polymerization of the solution has the structure:

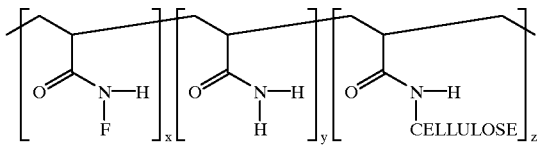

wherein:
F is the fluorescent indicator species;
CELLULOSE has the structure

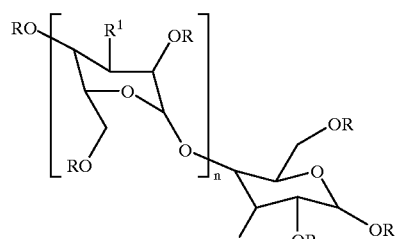

wherein each R is independently selected from the group consisting of H, $C_1$ to $C_6$ alkyl, $C_1$ to $C_6$ alkenyl, $C_1$ to $C_6$ alkynyl, and $C_1$ to $C_6$ esters, and $R^1$ is the acrylamide linkage to the copolymer backbone, —OR or $CH_2$=CH—(CO)—NH—;
n is in the range of about 2 to about 500;
x is in the range of about 1 to 30,000;
y is the range of about 1,000 to 50,000,000; and
z is in the range of about 1 to 1,000,000.

10. The method of claim 1, wherein the solution further comprises particles of a reflective material dispersed therein.

11. The method of claim 10, wherein the reflective material is selected from the group consisting of titanium dioxide, zinc oxide and barium sulfate.

12. The method of claim 11, wherein the reflective material is titanium dioxide.

13. The method of claim 1, further comprising applying a coating over the pH sensor means comprising a copolymer of (a) a cellulose acrylamide and (b) an acrylamide.

14. The method of claim 13, wherein the coating further comprises particles of a reflective material dispersed therein.

15. The method of claim 14, wherein the reflective material is selected from the group consisting of titanium dioxide, zinc oxide and barium sulfate.

16. The method of claim 15, wherein the reflective material is titanium dioxide.

* * * * *